(12) United States Patent
Shah et al.

(10) Patent No.: US 10,751,323 B2
(45) Date of Patent: *Aug. 25, 2020

(54) CONTROLLED-RELEASE MELATONIN COMPOSITIONS AND RELATED METHODS

(71) Applicant: Physician's Seal, LLC, Boca Raton, FL (US)

(72) Inventors: Syed M. Shah, Boca Raton, FL (US); Daniel Hassan, Boca Raton, FL (US)

(73) Assignee: Physician's Seal, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/298,552

(22) Filed: Mar. 11, 2019

(65) Prior Publication Data

US 2019/0269653 A1 Sep. 5, 2019

Related U.S. Application Data

(60) Continuation of application No. 15/412,963, filed on Jan. 23, 2017, now Pat. No. 10,226,647, which is a continuation of application No. 14/942,299, filed on Nov. 16, 2015, now Pat. No. 9,549,900, which is a division of application No. 14/186,599, filed on Feb. 21, 2014, now Pat. No. 9,186,351, which is a continuation of application No. 13/359,638, filed on Jan. 27, 2012, now Pat. No. 8,691,275.

(60) Provisional application No. 61/437,217, filed on Jan. 28, 2011.

(51) Int. Cl.
| | | |
|---|---|---|
| *A61K 31/4045* | (2006.01) | |
| *A61K 9/28* | (2006.01) | |
| *A61K 9/00* | (2006.01) | |
| *A61K 9/20* | (2006.01) | |

(52) U.S. Cl.
CPC ........ *A61K 31/4045* (2013.01); *A61K 9/0053* (2013.01); *A61K 9/2013* (2013.01); *A61K 9/2031* (2013.01); *A61K 9/2054* (2013.01); *A61K 9/2059* (2013.01); *A61K 9/2077* (2013.01); *A61K 9/28* (2013.01)

(58) Field of Classification Search
None
See application file for complete search history.

(56) References Cited

U.S. PATENT DOCUMENTS

| | | | | |
|---|---|---|---|---|
| 8,691,275 B2 * | 4/2014 | Shah | ................ | A61K 9/2013 |
| | | | | 424/484 |
| 9,186,351 B2 * | 11/2015 | Shah | ................ | A61K 9/2013 |
| 9,241,926 B2 * | 1/2016 | Shah | ................ | A61K 9/2013 |
| 9,549,900 B2 * | 1/2017 | Shah | ................ | A61K 9/2013 |
| 10,226,447 B2 * | 3/2019 | Shah | ................ | A61K 9/2013 |

* cited by examiner

*Primary Examiner* — Michael P Cohen
(74) *Attorney, Agent, or Firm* — Christopher M. Ramsey; GrayRobinson, P.A.

(57) ABSTRACT

An oral melatonin pharmaceutical dosage form that contains a sustained release dose of melatonin includes melatonin and an acid dispersed in a hydrogel-forming polymer matrix that combine after ingestion to form an acidic hydrogel containing the melatonin.

20 Claims, 4 Drawing Sheets

CONTROLLED-RELEASE MELATONIN COMPOSITIONS AND RELATED METHODS

CROSS-REFERENCE TO RELATED APPLICATIONS

This is a continuation of application Ser. No. 15/412,963, filed Jan. 23, 2017, now U.S. Pat. No. 10,226,447, which is a continuation of application Ser. No. 14/942,299, filed Nov. 16, 2015, now U.S. Pat. No. 9,549,900, which is a division of application Ser. No. 14/186,599, now U.S. Pat. No. 9,186,351, which is a continuation of application Ser. No. 13/359,638, now U.S. Pat. No. 8,691,275, which claims priority to provisional Application No. 61/437,217, filed Jan. 28, 2011. Each of these prior applications is incorporated by reference in its entirety.

FIELD

This relates to controlled-release melatonin compositions and related methods and, more particularly, to controlled-release melatonin compositions that include a controlled pH environment around the melatonin in the composition.

BACKGROUND

Melatonin is a hormone secreted by the pineal gland, a small pinecone-shaped gland located near the center of the brain. Its chemical formula is N-acetyl-5-methoxytryptamine, which is a derivative of the amino acid tryptophan and serotonin. The pineal gland secretes melatonin in a circadian rhythm—an approximately 24-hour cycle in the biochemical, physical or behavioral processes of an organism. A circadian rhythm is an endogenous or built-in function that is adjusted by environmental stimuli, such as daylight. It is known that the body plasma concentration of melatonin is low during the daytime, starts to rise during the late evening, and is maintained at 25-120 pg/mL during the night (over 8 hours) until it returns to the daytime baseline (Lee, 1995).

Exogenous, or synthetic, melatonin has been proposed to have clinical potential in human subjects to treat melatonin deficiency in the elderly, (Touitou, 2001) circadian rhythm disorders, including sleep disorders, jet lag, shift work syndrome, and seasonal affective diseases (Lee, 1995). Some suggest that melatonin may also be effective in the treatment of breast cancer, fibrocystic breast diseases, and colon cancer. Melatonin has been shown to modify the immune response, the stress response, certain aspects of the aging process, sleep disturbances in Alzheimer's patients, and oxidative stress. This suggests a plethora of beneficial uses for melatonin.

Exogenous melatonin treatments encounter several problems. Melatonin is eliminated from the blood quickly once administered. It has a plasma elimination half-life of less than one hour (Bénès, 1997). When administered orally, it shows low and variable bioavailability (Bénès, 1997). As with most oral administrations, it can take more than 30 minutes after ingestion for the blood plasma concentration of melatonin to reach its peak. This is partly due to the need for release of the melatonin from the dosage form followed by permeation through the wall of the gastrointestinal tract ("G.I. tract") for absorption to occur before the melatonin can enter the bloodstream.

Melatonin is slightly soluble, has good permeability characteristics, and is in the class II category according to the Biopharmaceutics Classification System (Tran, 2009). Therefore, the amount of melatonin available for absorption into the bloodstream primarily depends on its solubility. Melatonin's solubility generally decreases in less acidic environments. Because the pH of the gastrointestinal tract varies significantly, different amounts of melatonin are available for absorption into the bloodstream, depending on the region of the G.I. tract the melatonin enters.

Orally administered immediate and controlled-release melatonin formulations exist. Studies indicate large inter-subject variability of melatonin in the blood plasma of human subjects given melatonin orally (Bénès, 1997). Other problems reported include poor oral bioavailability and a nutritional status effect on the oral bioavailability (Bénès, 1997).

Various formulations of melatonin have been developed to provide release of melatonin over a 3 to 10 hour period to stimulate the natural (in vivo) release of melatonin. These formulations have not gained wide acceptance because of their variable response in patients. Patients may therefore experience middle of the night awakening, early morning grogginess, and sleep times of less than 5 hours.

Alternatives to conventional oral controlled-release dosage forms also exist. For example, a hydroxypropyl methylcellulose ("HPMC") matrix tablet was reported to release melatonin at a rate that was comparable to two commercially available products (Lee, 1999). In another example, the controlled-release characteristics of melatonin in a pH-responsive amphiphilic hydrogel with interpenetrating polymer networks was reported to be a function of the pH of the external environment of the tablet (Liu, 2006). Such controlled-release dosage methodologies remain in their infancy.

Several references in the patent literature also address melatonin formulations. For example, U.S. Pat. No. 5,498,423 and U.S. Patent Application Publication No. 2010/0119601, which are incorporated by reference herein, except to the extent that they are inconsistent with this application.

SUMMARY

A melatonin composition includes an oral melatonin pharmaceutical dosage form that contains a sustained release dose of melatonin. The dosage form includes melatonin and an acid dispersed in a hydrogel-forming polymer matrix that combine after ingestion to form an acidic hydrogel containing the melatonin. The dosage form is effective to release melatonin therefrom for at least six hours after oral ingestion

DETAILED DESCRIPTION OF EMBODIMENTS

In the Summary above and in the Detailed Description of Embodiments and in the accompanying drawings, reference is made to particular features including method steps. Where a particular feature is disclosed in the context of a particular aspect or embodiment, that feature can also be used, to the extent possible, in combination with and/or in the context of other particular aspects and embodiments.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art.

The solubility of some pharmacologically active substances is pH-dependent. When such a pharmacologically active substance is administered to a subject orally in a modified (sustained) release dosage form, the pH in and around the dosage form will vary significantly as the substance travels from the subject's mouth through the G.I. tract. As a result, the amount of the active substance released into the G.I. tract for absorption will also vary.

Melatonin, for example, which has been reported to have a pKa of approximately 4.4 to 4.7, will have different degrees of dissociation and different solubilities as it travels through the G.I. tract of the subject. In the gastric environment, at a pH range of approximately 1.0 to 3.0, its solubility is relatively high. In the upper G.I. tract environment, at a pH range of approximately 4.5 to 5.5, its solubility decreases. In the lower G.I. tract environment, at a pH range of approximately 5.5 to 7.0, its solubility decreases even further. This variability in the G.I. tract pH is not a major factor for conventional immediate-release dosage forms, as melatonin is readily dissolved in the low pH of the gastric environment. Unfortunately, this results in the melatonin being absorbed and eliminated too quickly to mimic the pattern of the endogenous melatonin found in healthy young subjects.

However, when a modified-release dosage form of melatonin is exposed to the low pH gastric environment, the melatonin is readily soluble and diffuses out of the dosage form at a faster rate due to a higher concentration gradient in and around the dosage form. Unfortunately, when the modified release dosage form reaches a higher pH environment further down the GI tract, the concentration gradient will be lower, resulting in a significantly lower release rate.

Therefore, the fact that conventional immediate and modified release melatonin compositions have a pH-dependent solubility profile means that there is variability in the release, absorption, and efficacy of the conventional melatonin treatments. The same is true for other active substances having a similar pH-dependent solubility profile that need to be delivered via modified release formulations.

One object of this invention is to provide a medicament composition that is adapted to release an effective amount of an active ingredient within the pH range found in the intestines continuously for 3 to 10 hours. When melatonin is the active ingredient, the composition may be used to treat disorders such as, for example, melatonin deficiency, sleep irregularities or circadian rhythm irregularities.

A medicament composition in accordance with the present invention comprises of one or more active ingredients, such as melatonin, one or more mechanisms for controlling the release rate of the melatonin, and controlled-release materials suitable for preparing a medicament composition that can be administered to a subject as a dosage form. In a particular embodiment, the controlled-release medicament compositions are adapted to release melatonin over a period of 3-10 hours after ingestion regardless of the pH environment the medicament composition encounters. Although melatonin is particularly useful in the invention, other active ingredients may include, but are in no way limited to Ramelteon i.e. (S)—N-[2-(1,6,7,8-tetrahydro-2H-indenol{5,4-b}furan-8-yl)ethyl]propionamide, Agomelatine i.e. N-[2-(7-methoxynaphthalen-1-yl)ethyl]acetamide, and TIK-301 i.e.B-methyl-6-chloromelatonin. Medicament compositions can be formulated into any solid form, such as tablet, capsule, granule, or liquid form, such as a suspension.

As used herein, unless the context requires otherwise, the term "melatonin" includes melatonin and chemical derivatives of melatonin.

Besides the examples provided below, embodiments of a medicament composition may comprise substances for the preparation of a final dosage form. Examples of these substances include one or more excipients, diluents, disintegrants, solvents, processing aids, buffering agents, colorants, flavorings, solvents, coating agents, binders, carriers, glidants, lubricants, granulating agents, gelling agents, polishing agents, suspending agent, sweetening agent, antiadherents, preservatives, emulsifiers, antioxidants, plasticizers, surfactants, viscosity agents, enteric agents, wetting agents, thickening agents, stabilizing agents, solubilizing agents, bioadhesives, film forming agents, essential oils, emollients, dissolution enhancers, dispersing agents, or combinations thereof.

Medicament compositions of the present invention may include controlled-released portions, expedited-release (burst) portions, or combinations thereof. Either portion is designed to release an active ingredient within certain conditions and/or over a certain time frame. The delayed-released portion is formulated to release an active ingredient in the pH environment of the G.I. tract and, further, over a certain period of time. The expedited-release portion is formulated to release an active ingredient into the upper digestive tract, such as into the stomach, for example. The expedited release portion may alternatively be achieved by tuning the size and shape of the dosage form to have enough surface area to release a desired amount of the active ingredient within a desired period of time.

Figure 1:
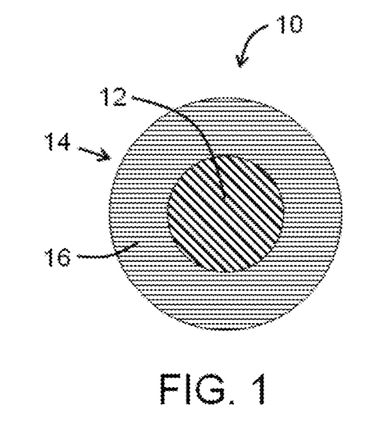
FIG. 1 is a cross-section diagram of an embodiment of a controlled-release unit of the present invention.

Referring initially to FIG. 1, a cross-section diagram of an embodiment of a controlled-release unit 10 of the present invention is shown. The controlled-release unit 10 in this embodiment may act as the delayed-release portion in certain embodiments of the medicament formulations. The controlled-release unit 10 includes at least one active unit 12 and one or more coatings 14. The coating 14 surrounds the active unit 12 and contains at least one layer. In this embodiment the coating 14 includes a controlled-release layer 16.

Figure 2:
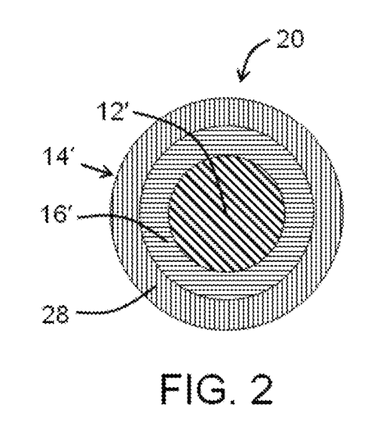
FIG. 2 is a cross-section diagram of an embodiment of a controlled-release unit of the present invention wherein the coating has more than one layer.

Referring to FIG. 2, a diagram of another embodiment of a controlled-release unit 20 is shown. The controlled-release unit 20 in this embodiment includes at least one active unit 12' and one or more coatings 14'. The coating 14' includes two layers. One layer is a controlled-release layer 16'. The other layer is a second layer 28. The second layer 28 surrounds the controlled-release layer 16'.

Referring continually now to FIGS. 1 and 2, one having ordinary skill in the art will recognize that each of these embodiments is merely shown as an example of certain embodiments. Details such as sizes, shapes, dimensions, relative dimensions and other details are not limiting. More than one active unit 12, 12' can be contained within the controlled-release unit 10, 20. Controlled-release units 10, may be in the form of multiparticulates or may be incorporated into a tablet.

The active unit 12, 12' contains one or more active ingredients. In some embodiments, the active unit 12, 12' contains a mixture of active ingredients. In some embodiments, the active unit 12, 12' may also contain one or more inactive ingredients, including, but in no way limiting, fillers, stabilizers, color coating, glidants and processing aids. Inactive ingredients and plasticizers can also be included in the coating 14, 14' or other portions of the medicament composition.

In the embodiment of FIGS. 1 and 2, the coating 14, 14' may include a single layer or multiple layers. At least one layer is a controlled-release layer 16, 16' which is adapted to provide a locally controlled pH environment around the active unit 12, 12'. The controlled-release layer 16, 16' is made of a material or combination of materials that include acidic moieties therein. The coating 14, 14' may further include materials for making the medicament composition into a dosage form such as a tablet, for example. In one embodiment, at least one constituent of the controlled-release layer 16, 16' is a material capable of forming a hydrogel. In another embodiment, at least one material in the coating 14, 14' is an enteric coating material. In one embodiment, at least one material in the coating 14, 14' is a sealant coating material.

In another embodiment, the controlled-release layer 16, 16' is a combination of one or more polymers, one or more acidic molecules, one or more acidic buffers or combinations thereof. The polymers can be selected from any number of pharmaceutically acceptable polymers such as the celluloses (e.g., carboxymethylcelluloses, methylcelluloses, hydroxypropylcelluloses, hydroxypropylmethylcelluloses); hyaluronates; alginates; polysaccharides, heteropolysaccharides (pectins); poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid; mixtures thereof, copolymers thereof, derivatives thereof, and the like. Examples of dispersing agents include, but are not limited to, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

Acidic molecules include organic and/or inorganic acidic molecules. Preferred organic acidic molecules include, but are in no way limited to, low molecular weight carboxylic acids such as citric acid, succinic acid and tartaric acid. Preferred inorganic acidic molecules include phosphoric acid and hydrochloric acid, but these examples are in no way limiting.

Acidic buffers can be prepared with organic or inorganic acidic molecules. Acidic buffers such as mono sodium citrate or phosphoric acid mono potassium salt are provided as preferred examples, but acidic buffers are in no way limited to these.

The controlled-release layer 16, 16' provides a locally acidic pH environment at the active unit 12, 12'. The locally acidic pH environment ensures that an effective amount of the active ingredient will be released continuously regardless of the external conditions. One particular embodiment of the controlled-release layer 16, 16' contains HPMC combined with one or more low molecular weight carboxylic acid molecules.

The active unit 12, 12', the controlled-release layer 16, 16' or both may comprise a surfactant adapted to enhance the aqueous solubility of melatonin. Preferred surfactants include, but are not limited to, polyethylene glycol (PEG) based surfactants. The molecular weight of PEG can be chosen to provide the desired properties of the composition. In one preferred embodiment, PEG 8000 is used.

Referring now to FIG. 2 only, the second layer 28 surrounds the controlled-release layer 16'. The second layer may be formulated to suit many functions. It can be adapted for the preparation of the medicament composition into a dosage form, such as a tablet, capsule, or granule, for example. Excipients used for forming such dosage forms are known in the art and can be employed here for forming the second layer 28. The second layer 28 may also be a seal coating formed from seal coating materials known in the art. The second layer 28 may be an enteric coating formed from enteric coating materials known in the art. The second layer may also comprise the expedited-release portion of the medicament formulation, which includes an active ingredient such as melatonin.

Embodiments of the present invention provide controlled and extended release medicament compositions containing melatonin as the active ingredient. One embodiment provides a sustained release of melatonin over a period of 3 to 10 hours in a manner that is reliable and not overly dependent of the pH found in the lumen of various sections of the G.I. tract. In this case, the controlled-release layer 16, 16' effectively insulates the melatonin in the active unit 12, 12' from the pH environment of the G.I. tract. Instead of dissolving directly into the G.I. tract, the melatonin dissolves within the controlled-release layer 16, 16' forming a concentration gradient across the controlled-release layer 16, 16'. Melatonin will then be released into the G.I. tract from the periphery of the controlled-release layer 16, 16' in this manner. This will ensure that the desired concentration gradient of the melatonin is maintained, irrespective of the pH of the lumen in the G.I. tract. The higher concentration of melatonin in the active unit(s) 12, 12' of the controlled-release unit 10, 20 will provide for a predictable release from the medicament composition.

Another aspect of certain embodiments is to provide a controlled-release medicament composition comprising an active ingredient combined with a pH lowering acid or acidic buffer, in a release controlling hydrogel matrix. In this embodiment, the medicament composition can be administered in a dosage form such as a tablet. The tablet can either be coated or not coated. To achieve this aspect of the invention, controlled-release units 10, 20 can be mixed with tableting materials into a tablet dosage form.

Figure 3:
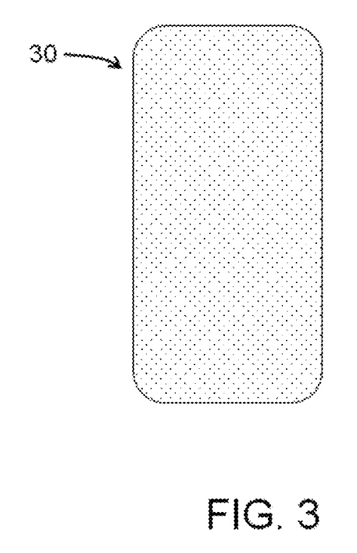
FIG. 3 is a diagram of an embodiment of a tablet of the present invention.

Referring to FIG. 3, a tablet 30 according to one embodiment of the present invention is shown. The shape of the tablet 30 is not limiting in any way. In one embodiment, a medicament composition comprises a tablet containing tableting materials, one or more active ingredients, a pH lowering acid or acidic buffer or combinations thereof and a hydrogel matrix. As an example, the tablet 30 can contain the controlled-release units 10, 20 according to the embodiments of FIGS. 1 and 2 or combinations thereof. The tablet 30 can also include one or more coatings (not shown) such as, by way of example only, an enteric coating, a seal coating, or combinations thereof.

In one embodiment of a tablet 30, an extended release formulation comprises melatonin, PEG8000, and citric acid. The PEG8000 aids in melatonin solubility and the citric acid creates a local environment with a pH lower than the pKa of melatonin. By keeping the pH of the local environment below the pKa of melatonin, melatonin is driven from the composition, preferably within 9 hours of ingestion so that patient does not feel lingering effects of melatonin after the nocturnal period. In vivo, the lower G.I regions of high pH will not markedly adversely affect the solubility (and resultant release) of melatonin in such an extended release formulation due to the local acidic environment in which the melatonin is carried.

Besides tablets, other medicament formulations are multiparticulate formulations comprising an active ingredient combined with a pH lowering acid or acidic buffer, in a release controlling hydrogel matrix. In this embodiment, the medicament composition can be administered in a dosage form such as a capsule by loading the multiparticulates into the capsule or combining them with tableting materials.

Variable dose medicament compositions according to embodiments of the present invention will now be described. For example, medicament compositions can be formulated to provide an initial dose of melatonin to induce sleep, followed by a sustained release of melatonin over the next 3 to 10 hours in a manner that is reliable and not overly dependent of the pH found in the lumen of various sections of the G.I. tract. The relative dosage percentage of the burst and the sustained release portion can vary. In some embodiments, the initial burst is up to 65% of the dose. In other embodiments, the sustained release portion is up to 90% of the dose. In one particular embodiment, the burst dose is approximately 50% of the melatonin in the formulation, which is released approximately in the first two hours after ingestion, and the sustained release portion is the remaining 50% of melatonin, which is released approximately over the next 5-8 hours. The rate of release can be controlled in several ways. The concentration of the active ingredient, such as melatonin, in the active unit 12, 12' can be adjusted. The pH of the containment layer 16, 16' can be adjusted by adding more or fewer acidic moieties. The thickness of the coating 14, 14' can be adjusted. A release-rate controlling film/membrane or a hydrogel matrix of a unit dosage form, like a tablet, can also be incorporated to control the release rate. If a tablet form is the final dosage form, the size and shape of the tablet can be adjusted to provide the preferred burst dose.

One variable dose medicament formulation according to an embodiment of the present invention provides a controlled-release medicament composition comprising a controlled-release portion and an expedited release portion. The controlled-release portion may include controlled-release units 10, 20, such as those shown in FIG. 1 or 2 or combinations thereof. The expedited release portion may be part of the controlled-release units 10,20, such as the second layer 28 of the controlled-release unit 20 in FIG. 2. Alternatively, the expedited release portion can be part of a tablet, such as the tablet 30 shown in FIG. 3. The expedited release portion can also be part of a bi-layer tablet.

Figure 4:
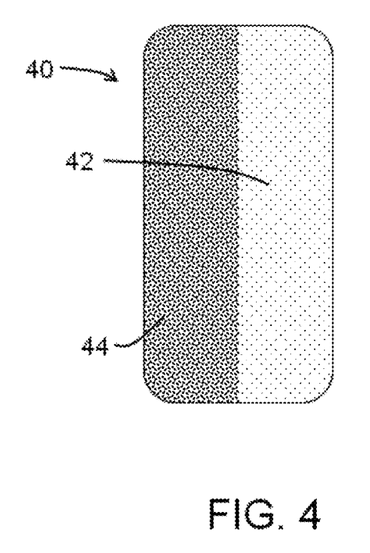
FIG. 4 is a cross-section diagram of an embodiment of a bi-layer tablet of the present invention.

FIG. 4 shows a cross-section of a bi-layer tablet 40 according to one embodiment of a melatonin medicament formulation, wherein the bi-layer tablet includes a controlled-release portion 42 and an expedited release portion 44. The expedited release portion is formulated to provide an initial burst dose of melatonin.

One embodiment of a variable dose medicament formulation includes melatonin in combination with a local pH lowering acid or acidic buffer along with a release controlling polymer, in the form of a tablet. The tablet is formulated so that between 10% to 50% of the melatonin is released from the expedited release portion within approximately 1-3 hours in an acidic dissolution medium and the remaining 50% to 90% of the melatonin in the delayed portion is released over the next 3 to 9 hours approximately.

In one embodiment, the bi-layer tablet 40 is formulated such that the expedited release portion contains from 10% to 50% melatonin, which is released within approximately 1-3 hours in an acidic dissolution medium. The controlled-release portion contains the remaining part of the melatonin in combination with a local pH lowering acid or acidic buffer along with a release controlling polymer, where the remaining portion of the melatonin (i.e. 50% to 90%), which is in the controlled-release portion, is released over the next 3 to 9 hours approximately.

Another embodiment provides a variable dose medicament composition comprising melatonin in combination with a local pH lowering acid or acidic buffer and a coating, having at least a first coating layer wherein the first coating layer maintains a low pH inside the controlled-release unit and also serves as a release rate controlling membrane. The coating may further include a second coating layer that contains a portion of the melatonin. The second coating provides an expedited release of the melatonin.

Figure 10:
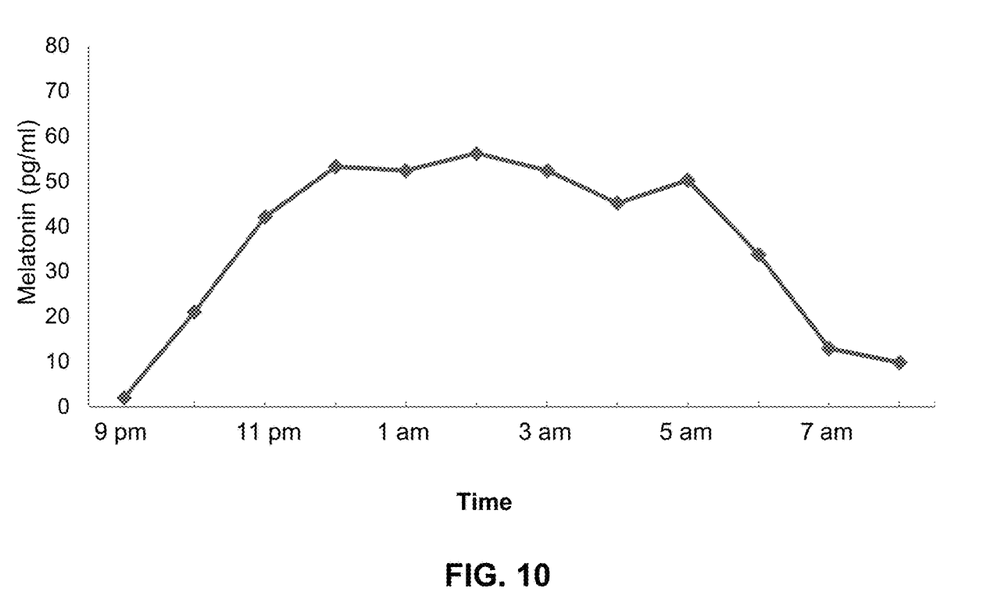
FIG. 10 is a graph of the nocturnal plasma profile of melatonin concentration in a healthy adult human. This profile exemplifies the profile to be substantially simulated in accordance with a preferred embodiment of the invention.

FIG. 10 illustrates the average normal human plasma melatonin levels throughout the body as a function of time and is derived from (McIntyre, 1987), which is incorporated by reference herein in its entirety. The illustrated rise and decline of circulating melatonin occurs after sunset and before sunrise, respectively. Maximal melatonin levels in a person with a normal melatonin profile are typically about 60±20 pg/ml. In order to affect the brain by exogenous melatonin, it is desirable to elevate the plasma melatonin concentration so as to simulate the amounts present at night in the brain of a person with a normal endogenous melatonin profile. It is therefore desirable for embodiments of an extended release melatonin formulation to, upon administering such a formulation to a human subject, to achieve a rapid melatonin rise (1-2 hours) in plasma melatonin concentration that plateaus at a concentration of 60±20 pg/ml for about 6 to 7 hours, followed by a rapid melatonin decline (1-3 hours) of plasma melatonin to about pre-rise levels.

Referring to FIG. 2, the first coating layer can be the controlled-release layer 16'. The second coating layer can be the second layer 28. In this embodiment, the controlled-release unit forms a variable dose granule. In alternative embodiments, the expedited release portion may be provided in combination with the coated granule as a powder blend.

Accordingly, many different variable dose melatonin medicament formulations can be prepared. Several specific examples will now be provided, however, these examples are not an exhaustive list.

An embodiment of a variable dose medicament formulation includes a bi-layer tablet 40 containing controlled-release units 10.

Another embodiment of a variable dose medicament formulation includes a tablet 30 containing controlled-release units 10 wherein the expedited release portion is formulated into the tablet 30. Another embodiment of a variable dose medicament formulation includes a tablet 30 containing controlled-release units 20, wherein the expedited release portion is the second layer 28.

Another embodiment of a variable dose medicament formulation includes a capsule loaded with controlled-release units 20 in a granular form, wherein the expedited release portion is the second layer 28.

Another embodiment of a variable dose medicament formulation includes a bi-layer tablet 40 containing controlled-release units 20.

Other embodiments of variable dose medicament formulation include combinations of controlled-release units and controlled-release units 20 prepared into tablet 30, bi-layer tablet 40 or capsule dosage forms.

According to another aspect of the invention, methods of making melatonin medicament compositions according to embodiments of the present invention will now be described. The methods may be embodied in many different forms. Only certain embodiments are described below by way of example.

In general, melatonin medicament compositions can be made in many different ways. These include wet granulation processes, such as aqueous granulation processes, or dry granulation processes, where dry powder based blending process is followed by direct compression, or with an intermediate roller compaction step or a combination thereof.

One general embodiment of the method for making a melatonin medicament composition comprises dry blending the active ingredient with at least one polymer suitable for forming the controlled-release layer 16, 16' and conventional processing aids plus optional fillers. Conventional processing aids include but are in no way limited to magnesium stearate, stearic acid, talc, sodium lauryl sulfate. Optional fillers include but are in no way limited to complex silicates, calcium carbonate, glycine, dextrin, sucrose, sorbitol, dicalcium phosphate, calcium sulfate, lactose, kaolin, mannitol, sodium chloride, talc, dry starches and powdered sugar. The optional binder may be selected from among known binders, including, but not limited to, cellulose, and povidone, among others. In one embodiment, the binder is selected from among microcrystalline cellulose, crospovidone, and mixtures thereof. The dry blend can then be formed into a typical dosage form for oral administration. In a preferred embodiment, at least one of the polymers forms a hydrogel.

In a more particular embodiment, the method for making a melatonin medicament composition comprises dry blending melatonin with the powder form of an acidic compound or acidic buffer, HPMC and, optionally, conventional processing aids and fillers. The dry blend can then be directly compressed into a typical tablet dosage form for oral administration.

In order to prepare a solid dosage form such as a tablet, excipients known in the tableting arts can be employed.

In one embodiment, melatonin and/or one or more other active ingredients are provided as a combination of an expedited release portion plus a controlled-release portion. The expedited release portion may be present as a coat, powder, or as a readily dissolvable amount of active ingredient on the surface of the controlled-release portion. Here, the controlled-release portion comprises melatonin plus one or more active ingredients in combination with an acidic compound or acidic buffer.

This composition allows for targeted release of melatonin and one or more active ingredients from the expedited release portion into the acidic gastric environment of the patient and for targeted release of the melatonin and one or more active ingredients from the controlled-release portion into the lower gastrointestinal tract; for example into the small intestine, the large intestine, the colon and/or the rectum. In certain embodiments, the controlled-release portion comprising the active ingredient further includes an enteric or pH-dependent coating such as cellulose acetate phthalates and other phthalates. Examples include, but are in no way limited to polyvinyl acetate phthalate, methacrylates, and Eudragit® polymers. Alternatively, the controlled-release portion provides controlled-release to the small intestine and/or colon by the provision of pH sensitive methacrylate coatings, pH sensitive polymeric microspheres, or polymers which undergo degradation by hydrolysis. The controlled-release composition can be formulated with hydrophobic or gelling excipients or coatings. Colonic delivery can further be provided by coatings which are digested by bacterial enzymes such as amylose or pectin, by pH-dependent polymers, by hydrogel plugs swelling with time (Pulsincap), by time dependent hydrogel coatings and/or by acrylic acid linked to azoaromatic bonds coatings.

In certain embodiments the controlled-release portion comprises hypromellose (HPMC), microcrystalline cellulose, and a lubricant. The mixture of melatonin, an acid or acidic buffer, hypromellose and microcrystalline cellulose may be formulated into a tablet or capsule for oral administration. In certain embodiments, the mixture is granulated and pressed into tablets.

In other embodiments, the controlled-release portion of the present invention is provided in a multiparticulate formulation. A mixture of melatonin in combination with an acidic compound or acidic buffer plus a suitable polymer is granulated to form pellets which are coated.

In certain embodiments, the pellets are seal coated with a non-functional coating. In other embodiments, the pellets are first seal coated with a non-functional coating and then coated with a functional coating.

As used herein the term "non-functional coating" is a coating that does not affect the release rate of the drug. Examples of a non-functional coating include hydroxypropyl cellulose, hypromellose or polyvinyl alcohol. In certain embodiments, the non-functional coating is Opadry® Clear, which contains, hydroxypropyl methylcellulose and polyethylene glycol.

As used herein, the term "functional coating" is a coating that affects the release rate of the drug from the dosage form. Examples of a functional coating include ethylcellulose and polymethacrylate derivatives (Eudragit® polymers).

Accordingly, another embodiment provides a mixture of multiparticulate formulations, comprising pellet cores containing the active ingredient in combination with an acidic compound or acidic buffer plus a non-functional seal coating serving as the expedited release portion mixed with seal coated cores which have been further coated a functional seal coating for controlled-release.

In the embodiment for the multiparticulate formulations, the expedited release portion may be part of the functional seal coated formulation as a free flowing powder blend containing the active ingredient or it is coated on the surface of the functional coat.

Certain embodiments of methods of using of the melatonin medicament composition will now be described. These methods may be embodied in many different forms. Only certain preferred embodiments are described below.

In one embodiment of the method of use, an effective dose of a melatonin medicament composition comprising at least one controlled-release unit, such as a controlled-release unit 10,20 shown in one or more of the embodiments of FIGS. 1 through 4, is administered to a subject in need thereof.

In another embodiment of the method of use, an effective dose of a medicament composition comprising at least one controlled-release unit, such as a controlled-release unit 10,20 shown in one or more of the embodiments of FIGS. 1 through 4, is administered to a subject in need thereof. In this embodiment, the active unit 12, 12' contains melatonin.

In another embodiment of the method of use, an effective dose of a medicament composition comprising at least one controlled-release unit, such as a controlled-release unit 10,20 shown in one or more of the embodiments of FIGS. 1 through 4, is administered to a subject in need thereof. In this embodiment, the active unit 12, 12' contains at least melatonin and at least one or more of the following substances: HPMC, citric acid, monosodium citrate, tartaric acid, monosodium tartrate, phosphoric acid, and monosodium phosphate.

In another embodiment of the method of use, an effective dose of a medicament composition comprising at least one controlled-release unit, such as a controlled-release unit 10,20 shown in one or more of the embodiments of FIGS. 1 through 4, is administered to a subject in need thereof. In this embodiment, the active unit 12, 12' contains at least melatonin and at least one or more of the following substances: HPMC, citric acid, monosodium citrate, tartaric acid, monosodium tartrate, phosphoric acid, and monosodium phosphate. Here, the medicament composition is administered to a subject as a sleep aid.

In another embodiment, the method of use comprises administering and/or ingesting a melatonin medicament composition of the present invention, permitting a part of the active ingredient(s) to be released in the stomach and allowing the melatonin medicament composition to enter the small intestine and permitting the remaining active ingredient(s) to be released into the small intestine in a controlled manner.

In another embodiment, the method of use comprises administering and/or ingesting a melatonin medicament composition of the present invention, allowing the melatonin medicament composition to enter the small intestine, and permitting the active ingredient(s) to be released into the small and/or large intestine in a controlled manner.

An effective amount of melatonin is a quantity sufficient to affect a condition in the subject, such as affecting sleep, a disease, or process in the body of the subject. In some preferred embodiments, an effective amount can vary from 5 micrograms to 10 milligrams of melatonin.

EXAMPLES

This section describes a few specific examples of multiparticulate formulations of the invention and the methods by which they were made. These examples are presented by way of example only and are not intended to limit the scope of the invention.

1. Preparation of a Tablet Medicament Formulations

A. Experimental Details.

Melatonin (Nutri-Force, lot number 81120) was used in the following experiments. The melatonin was reported to be a micronized grade. Shipment, handling and processing of melatonin and prototypes were all under ambient room temperature. In-process materials and bulk tablets were stored in double polyethylene bags with desiccant. Melatonin was evaluated for appearance and particle size by sieve analysis.

Melatonin was visually characterized as a white to off-white poor flowing, fine powder. The particle size sieve analysis of melatonin revealed a non-Guassian distribution of particles predominately of 150 microns. Manufacture of the melatonin controlled-release tablets dissolves the melatonin in a solution of polyethylene glycol and water as part of the granulation fluid. Therefore, the particle size of the melatonin has no substantial effect on the final properties of the tablet, but did influence the rate at which the melatonin was dissolved during manufacture.

The following equipment was used preparing the formulations: Kitchen Aide planetary mixer; hot plate/magnetic stirrer; #6, 20 and 40 mesh sieves; tray drying oven; comil with 0.039" round hole screen; Piccola B/D 8 station R&D press 0.455"×0.190" capsule shaped tooling; Computrac LOD instrument; tablet hardness tester; tablet friability tester; and calipers.

B. Development of 2 mg Melatonin Controlled-Release Tablets.

This section describes the development of prototype tablets in accordance with the invention. A hypromellose based monolithic tablet was utilized to achieve the targeted 6-8 hours extended release of the 2 mg melatonin. The formulation was varied as presented in Table 1 to identify a formulation with the targeted release profile. The tablet size was held constant throughout the experimentation at 250 mg with a strength of 2 mg melatonin per tablet. The formulations were prepared in small 200-300 g batches.

Figure 5:
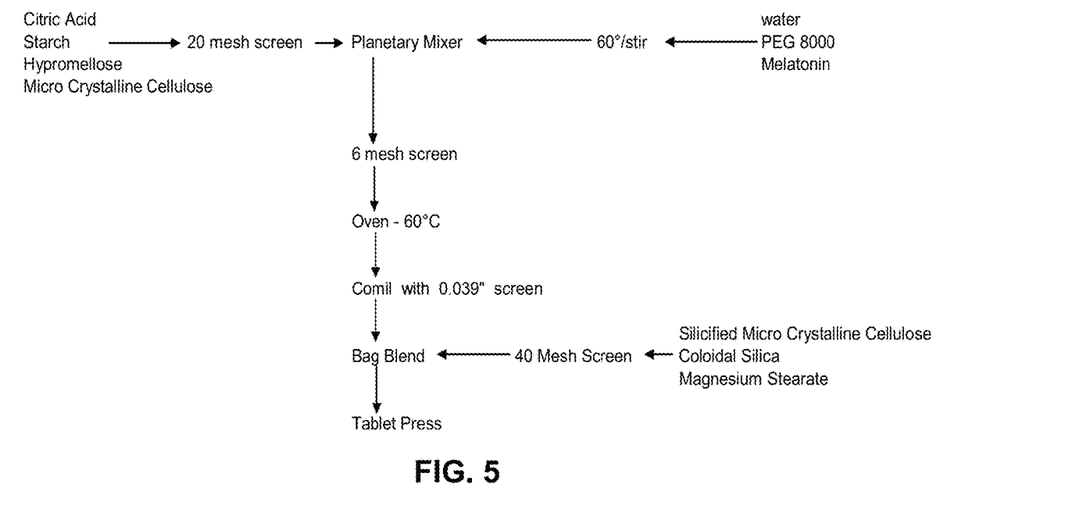
FIG. 5 is a flow diagram illustrating an embodiment of a low shear granulation process.

It was discovered that hypromellose exhibited undesirable flow characteristics. For this reason, a granulation process was used. The prototypes were manufactured using a low shear wet granulation process in a planetary mixer. The intra-granular components were charged to the mixing bowl and granulated either with water in the early prototypes or a solution of water, polyethylene glycol and melatonin in the later prototypes. The wet granulation was wet milled through a 6 mesh hand sieve to break up any large agglomerates and then oven tray dried at 60° C. to a ~1-3% moisture level. The dried granulations were milled to size with a Comil cone type mill using a 0.55" screen initially and later a 0.039" screen. The extra-granular excipients were bag blended into the milled granulation and the final blend was compressed on a Piccola tablet press using 0.455"×0.190" capsule shaped tooling to a tablet weight of 250 mg and hardness of ~5 kp. The process used for the lead prototype lot CYV45-002-048A is summarized in the flow diagram of FIG. 5.

Analysis of Prototypes.

A two stage dissolution procedure in a USP dissolution apparatus type III with 2 hour in 0.1 N hydrochloric acid followed by 12 hours in pH 6.8 phosphate buffer was used to evaluate the prototypes. This was later simplified to a single stage procedure in 0.9% saline when the two methods were shown to give equivalent results. Melatonin assay and related substance testing was performed by HPLC on the identified lead prototype, which was CYV45-002-48A.

Figure 6:
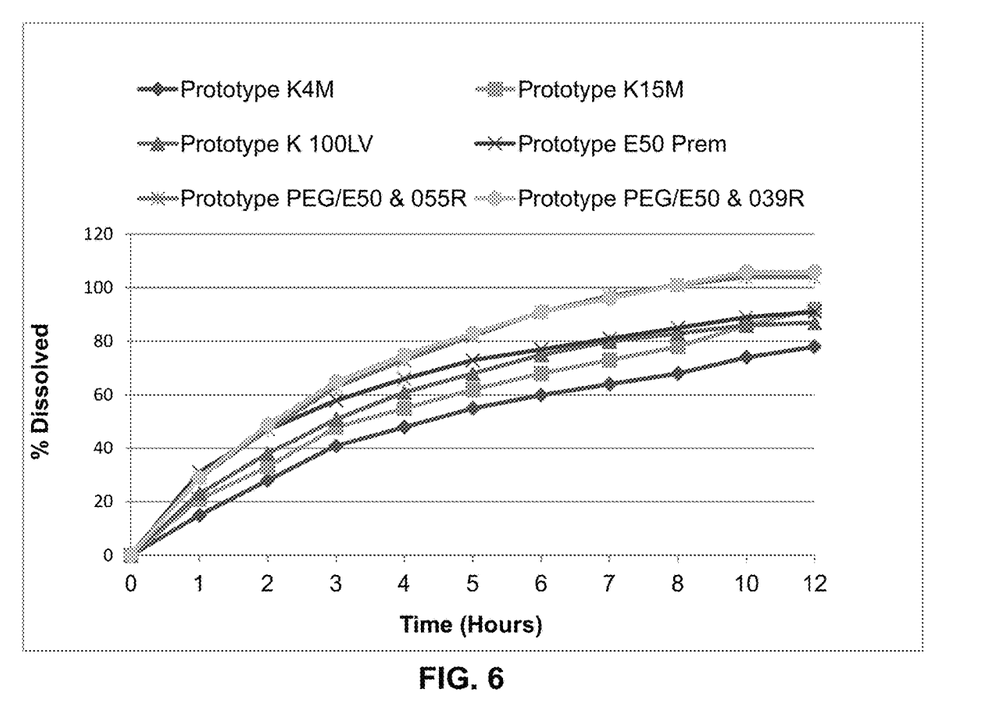
FIG. 6 is a graph of the dissolution profile of embodiments of melatonin compositions of the invention.

Four different matrix forming hypromellose grades of varying molecular weight (K4M, K15M, K100LV and E50) were initially screened (Lots CYV45-002-004, 007, 011 and 012) as presented in Table 1. The hypromellose E50 hypromellose proved to be the most promising of the polymers evaluated, but it still released the melatonin slower than desired. The dissolution results are presented in FIG. 6.

Citric acid was first included in the formulation at a concentration of 16% but was increased to approximately 30% to maintain a low pH in the tablet matrix, enhancing the aqueous solubility of the melatonin. StarCap 1500 starch was initially added at a concentration 28% but was reduced to 12% to make room for the added citric acid without increasing tablet size.

The aqueous solubility of the melatonin was further increased, by dissolving the melatonin in a 50% solution of polyethylene glycol surfactant (PEG 3350) and spraying the solution into the granulation. The use of the PEG 3350 successfully increased the dissolution rate.

Concurrently, the effect of granulation particle size on the dissolution was evaluated by using a Quadro Comil with either a 0.055" or 0.039" round hole screen (lot CYV45-002-021A and B). The particle size of the granulation had little effect on dissolution rate but the smaller particle size granules was observed to generate less inter-tablet variability in the dissolution data. As a result, the use of the 0.039" screen was adopted for use in subsequent trials.

It was discovered that compression of the tablets with the PEG 3350 was not ideal. Sticking in the cups of the tablet punches was noted causing cosmetic defects, erratic tablet weight and hardness. To alleviate the sticking problem, higher molecular weight PEG 8000 was substituted for the use of the PEG 3350 in the formulation (lot CYV45-002-030).

Figure 7:
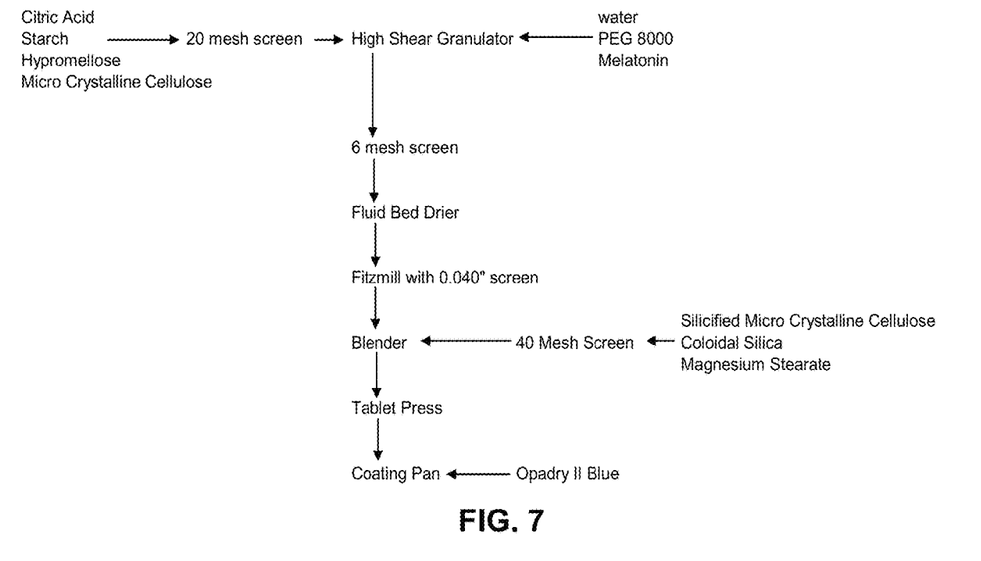
FIG. 7 is a flow diagram illustrating an embodiment of a high shear granulation process for the manufacture of extended-release melatonin tablets.

The batch was also scaled up to a 1 kg size and processed using a high shear granulator and fluid bed in place of the low shear planetary mixer and tray drying oven used previously. This was done to provide ample material to compress for an extended period to investigate the tablet sticking issue and adapt the process to be more suitable for future manufacturing. The scaled up process is summarized in the flow chart of FIG. 7. The equipment used in the scaled up process included the following: Fielder PP1 High Shear granulator; Niro-Aeromatic MP-1 Multi-processor; Fitzmill J mill equipped with a 0.040 round hole screen; 2 Qt PK Blender; Piccola Eight Station B/D tablet press; 0.1920"× 0.4570" capsule shape tooling embossed with "REM" embossed in upper punch; Accela-cota model 24MK III (24" coating pan; hot plate; Overhead mechanical lab stirrer and propeller; and 20 mesh, 6 mesh and 40 mesh sieves.

The tablets were also film coated with an Opadry II Blue non-functional coating to simulate the eventual final product that was desired. The granulation, blend and tablets processed well at the increased scale using the high shear granulation process. The sticking problem during tablet compression was alleviated. Coating was conducted successfully with no difficulties. It was discovered that melatonin dissolution was undesirably retarded by the substitution of PEG 8000 for PEG 3350. Accordingly, the formulation was tweaked to optimize the melatonin dissolution.

Figure 8:
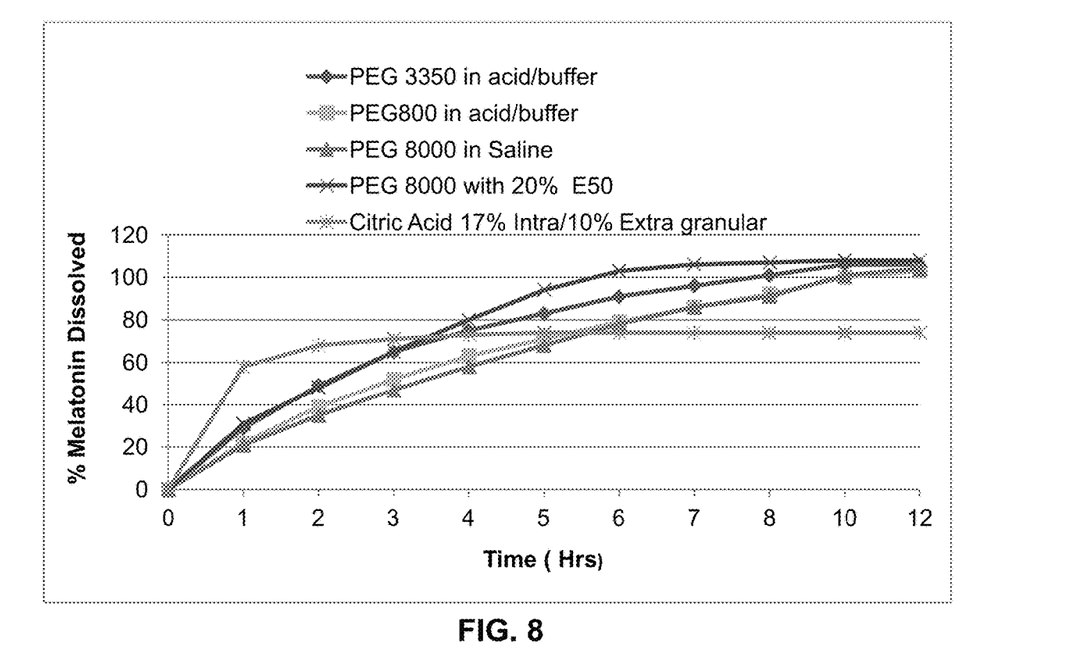
FIG. 8 is a graph of the dissolution profile of an embodiment of an extended-release melatonin tablet.

To compensate for the slower release of melatonin, a small trial formulation with PEG 8000 (lot CYV45-002-048B) was made shifting a portion of the intra-granular citric acid to extra-granular to increase dissolution by increasing the porosity of the tablet matrix. Also, a small trial batch (lot CYV45-002-048A) utilizing the PEG 8000 but reducing the concentration of the matrix forming polymer hypromellose E50 from 30% to 20% was made and evaluated. The tablet weight was held constant by adding additional extra-granular ProSolv which also increased the hydrophilicity of the tablet to accelerate the release of the melatonin. Both approaches increased dissolution rate. Lot CYV45-002-048A with reduced level of E50 (20%) best fit the target dissolution profile (FIG. 8). Table 2 lists the ingredients in this formulation.

Figure 9:
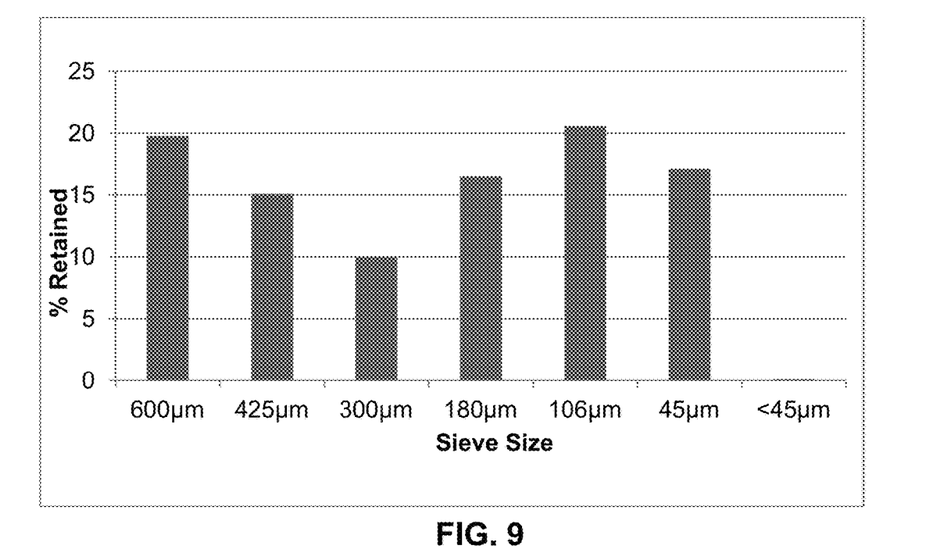
FIG. 9 is a graph of the particle size distribution of an embodiment of a high shear granulated melatonin placebo blend.

The physical properties of the final blend and compressed tablets for the CYV45-002-048A prototype are presented in Tables 3 and 4 and FIG. 9. The particle size of the final blend is non-Guassian and somewhat bi-modal. The flow of the final blend was acceptable as indicated by a blend compressibility of 14% and Flodex critical orifice value of 16 mm. The formulation is preferably compressed with tablet presses utilizing a paddle feeder to ensure good flow and ensure that particle size segregation does not occur in the press feed frame.

The compressed tablets had low tablet weight variation. Tablet hardness and thickness also exhibited low variability. The mean tablet hardness was 3.9 kp with a range of 3.4-4.2 kp. At first glance, this would appear to be low tablet hardness; however, this provided a robust tablet with extremely low friability (0.03% lost in 100 drops) suitable for coating in a tablet coating pan. Because the tablets comprised both PEG and citric acid, the tablets were soft due to plastic deformation; however, this softness is advantageous as it imparts a high degree of impact resistance. The capsule-type shape of the tablets itself with a low cross-sectional area generates deceptively low tablet hardness values.

Prototype Lot CYV45-002-048A was assayed for melatonin and related substances and the results are presented in Table 5. The high assay value of 105.2% can largely be explained as a result of loss of moisture during the granulation drying process. The excipients and melatonin prior to granulation contained 5.1% moisture as determined in a baseline loss on drying evaluation but only contained 1.2% after the granulation was dried; thereby, making the granulation 3.9% super-potent. The granulation moisture will preferably be dried to level approximate to the baseline moisture in future batches.

Because maintaining a low pH in the tablet matrix over the course of the release was a desired property, tablets of CYV45-002-048A were placed in dissolution baths containing saline for up to 7 hours at 50 rpm paddle speed. The "ghost" cores remaining after 7 hours were decanted away and pH of the tablet cores was determined. At 4 hrs the pH was determined to be 2.5 and at 7 hrs it was 2.8. This indicates that citric acid remained in the tablet for an extended period of time to lower the pH and assist in the solubilization of the melatonin.

Preparation of Final Tablet.

The formulation development activities successfully identified a controlled-release prototype for 2 mg dose strength melatonin tablet. The in-vitro dissolution release profile met the desired objective of releasing half the melatonin with 1-2 hours followed by first order release with greater than 90% release achieved at 6 hours. The release of melatonin was shown to be independent of the pH of the dissolution media with similar profiles generated using an acid/pH 6.8 two stage dissolution versus a single stage saline method. The in-vitro dissolution data suggests the tablets will release melatonin quickly to induce sleep and maintain a level of melatonin for up to 6 hours with little melatonin remaining to create grogginess upon awakening. The formulation utilizes GRAS excipients and can be manufactured by a high shear wet granulation process suitable for manufacture in a production facility.

Using the experimental results described above, a final tablet comprising melatonin was prepared. The final tablet comprises the ingredients shown in Table 6 and was prepared according to the procedure that will now be described.

A granulation solution was first prepared by:
(a) charging 58.0 g of purified water to a beaker and heating to approximately 60° C.;
(b) stirring and dissolving 50.0 g of PEG 8000 in the solution of (a);
(c) dissolving 8.0 g of melatonin in the solution of (b), resulting in a clear amber solution; and
(d) allowing the solution of (c) to cool to room temperature.

High shear wet granulation and wet milling was next performed by:
(a) screening the microcrystalline cellulose, citric acid and hypromellose through a 20 mesh sieve and charge to a Niro PP-1 high shear granulator;
(b) mixing the materials in the granulator for approximately three minutes at a speed of 300 rpm;
(c) continued mixing and sprayed the granulation solution on the mixing materials over the course of about 3 minutes;
(d) while continuing mixing, spraying and additional 157 g of water over the course of approximately 5 minutes;
(e) wet massing the granulation by mixing and additional 2-3 minutes; and
(f) discharging the product of (e) from the granulator and sizing the granulation through a 0.156" square hole screen using a Quadro Comil.

Drying granulation and dry milling was next performed by:
(a) charging the wet milled granulation to a Niro MP-1 fluid bed dryer and drying at an air inlet temperature of 60° C.;
(b) drying the product of (a) to approximately 2% moisture content (as determined by an LOD loss on drying instrument—the drying time was approximately 25 minutes);
(c) passing the product of (b) through a Fitzmill J mill at a slow speed in the knives forward mode using a 0.040" round hole screen Final blending was achieved by:
(a) charging the dried milled granulation to a 2 quart V-blender;
(b) screening the Cabosil colloidal silicon dioxide through a 20 mesh sieve and charging to the blender;
(c) blending the product of (b) for 120 revolutions;
(d) screening the magnesium stearate through a 40 mesh sieve and charging to the blender; and
(e) blending the product of (d) for 72 revolutions.

The final blend was compressed into a tablet by:
(a) equipping a Piccola BD 8 station rotary tablet press with 0.1920"×0.0.4570" capsule shaped tablet tooling;
(b) loading the tablet press with the final blend; and
(c) compressing tablets to the following targets: tablet weight=250 mg, tablet hardness=8 kp, tablet thickness=0.185."

The present invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

Moreover, it should also be understood that any measurements, quantities or numerical figures expressed herein are intended to be approximate and not an exact or critical figure unless expressly stated to the contrary.

Further, any publications, patent applications, patents, and other references mentioned herein are incorporated by reference in their entirety as if they were part of this specification. However, in case of conflict, the present specification, including any definitions, will control. In addition, as noted above, materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

TABLE 1

Formulations of 2 mg Melatonin Extended Release Tablet Development Prototypes

| | | % w/w Lot # CYV45-002- | | | | | | | |
|---|---|---|---|---|---|---|---|---|---|
| | Ingredient | 004 | 007 | 011 | 012 | 21A/B | 030 | 48A | 48B |
| Intra-granular Components | Melatonin (2 mg/tablet) | | | | | 0.8 | | | |
| | Hypromellose K4M | 30 | | | | | | | |
| | Hypromellose 15M | | 30 | | | | | | |
| | Hypromellose K100LV | | | 30 | | | | | |
| | Hypromellose E50 | | | | 30 | 30 | 30 | 20 | 30 |

TABLE 1-continued

Formulations of 2 mg Melatonin Extended Release Tablet Development Prototypes

| | Ingredient | % w/w Lot # CYV45-002- | | | | | | | |
|---|---|---|---|---|---|---|---|---|---|
| | | 004 | 007 | 011 | 012 | 21A/B | 030 | 48A | 48B |
| | PEG 3350 | | | | | 5 | | | |
| | PEG 8000 | | | | | | 5 | 5 | 5 |
| | Citric Acid | 16 | 16 | 32 | 32 | 27 | 27 | 27 | 17 |
| | Starch | 28 | 28 | 12 | 12 | 12 | 12 | 12 | 12 |
| | MCC | | | | | 12.2 | | | |
| Extra-granular Components | ProSolv HD90 | 12 | 12 | 12 | 12 | 12 | 12 | 22 | 12 |
| | Citric acid | | | | | | | | 10 |
| | Cabosil | | | | | 0.5 | | | |
| | Mag Stearate | | | | | 0.5 | | | |
| | Total | | | | | 100% | | | |

TABLE 2

Quantitative Formula for Melatonin 2 mg ER Tablets Lead Prototype Lot # 11216-048A

| | Materials Vendor/Lot # | Functionality | 2 mg Tablet | % w/w | g/Batch |
|---|---|---|---|---|---|
| Gran. Soln | Melatonin (Nutri-Force lot # 81120) | melatonin | 2.0 | 0.8 | 2.4 |
| | Purified Water[1] | Granulation solvent | NA | NA | 15 g for PEG solution + 33.5 g for granulation |
| | Polyethylene Glycol PEG8000 (Dow) | Solubilizer | 12.5 | 5.0 | 15 |
| Intragranular | Microcrystalline Cellulose, NF Avicel PH-101 (FMC) | Diluent | 30.5 | 12.2 | 36.6 |
| | Citric Acid Monohydrate Powder (Spectrum) | Acidifier | 67.5 | 27.0 | 81 |
| | Co-processed Starch Starcap 1500 (Colorcon) | Diluent/binder | 30 | 12.0 | 36 |
| | Hypromellose Methocel ™ E50 (Dow) | Matrix Polymer | 50.0 | 20.0 | 60 |
| Extragranular[2] | ProSolv HD90 (JRS Pharma) | Diluent | 55.0 | 22.0 | 66 |
| | Cab-O-Sil M-5P (Cabot) | Glidant | 1.25 | 0.5 | 1.5[b] |
| | Magnesium Stearate (Veg. Source, Product Code 2257), NF/EP/JP | Lubricant | 1.25 | 0.5 | 1.5[b] |
| | Total | | 250.0 | 100.0% | 300 g |

[1]Removed upon drying
[2]Adjusted based on granulation yield

TABLE 3

Melatonin 2 mg Extended Release Prototype Final Blend Physical Properties

| Bulk Density | 0.43 g/mL |
|---|---|
| Tap Density | 0.50 g/mL |
| Compressibility | 14.4% |
| Flodex Flow | 16 mm critical orifice |
| Sieve Analysis | % Retained |
| 600 μm | 19.8 |
| 425 μm | 15.1 |
| 300 μm | 10.0 |
| 180 μm | 16.5 |
| 106 μm | 20.6 |
| 45 μm | 17.1 |
| <45 μm | 0.1 |

TABLE 4

Properties of Melatonin 2 mg Extended Release Tablet-Prototype Lot CYV45-002-048A

| Property | Results |
| --- | --- |
| Tablet Press | Eight station Picolla B/D press (one station used) |
| Tablet Tooling | FDL-041: 0.455" × 0.190" capsule shaped, plain faced |
| Tablet Press Speed | 40 rpm |
| Main compression Force | 4.2 kiloNewtons |
| Precompression | Not used |
| Ejection Force | 92 Newtons |
| Mean Tablet weight* | 251 mg (range 249-253 mg % RSD = 0.5) |
| Mean Tablet Hardness* | 3.9 (range 3.4-4.2, % RSD = 6.2) |
| Mean Tablet Thickness* | 0.196" (range 0.195-0.196", % RSD = 0.2) |
| Tablet Friability | 0.03% for 100 drops |

*10 tablets chosen at random from compression of 300 g batch

TABLE 5

Melatonin Assay/Related Substances of 2 mg Melatonin Extended Release Tablets Lot CYV45-002-048A

| | |
| --- | --- |
| Melatonin Assay | 105.2% |
| Reportable Impurities (>0.10%) | 0.18% @RRT 1.47 |
| Total Impurities | 1.8% |

TABLE 6

Composition of Final Tablet

| Materials Vendor/Lot # | 2 mg Tablet | % w/w | g/Batch |
| --- | --- | --- | --- |
| Purified Water | NA$^a$ | NA$^a$ | 58 g for PEG solution + 157 g for granulation$^a$ |
| Melatonin | 2.0 | 0.8 | 8.0 |
| PEG8000 | 12.5 | 5.0 | 50.0 |
| Microcrystalline Cellulose, NF Avicel PH102 | 144.25 | 57.7 | 577.0 |
| Citric Acid Powder | 12.5 | 5.0 | 50.0 |
| Hypromellose Methocel ™ E50 | 75.0 | 30.0 | 300 |
| Cab-O-Sil Colloidal Silicon Dioxide | 1.25 | 0.5 | 5.0 |
| Magnesium Stearate | 2.50 | 1.0 | 10.0 |
| Total Prior to Coating | 250.0 | 100.0% | 1000 g |

$^a$Water was used as a solvent and granulation fluid and was removed during processing.

BIBLIOGRAPHY

Bénès, L., B. Claustyat, et al. (1997). "Transmucosal, oral controlled release, and transdermal drug administration in human subjects: A crossover study with melatonin." *J Pharmaceutical Sci.* 86(10): 1115-1119.

He, H., Katsumura, Y. et al. (2005). In Japanese. *Org. and Biomol. Chem.*, 3 (2005) 1568

Lee, B.-J., Keith Parrott, et al. (1995). "Design and evaluation of an oral controlled release delivery system for melatonin in human subjects." *Int J Pharmaceuticals* 124(1995): 119-127.

Lee, B.-J., S.-G. Ryu, et al. (1999). "Formulation and release characteristics of hydroxypropyl methylcellulose matrix tablet containing melatonin." *Drug Dev. and Ind. Pharmacy* 25(4): 493-501.

Liu, Y.-Y., X. D. Fan, et al. (2006). "pH-responsive amphiphilic hydrogel networks with IPN structure: A strategy for controlled drug release." *Int. J Pharmaceutics* 308 (2006): 205-209.

McIntyre I. M, Norman, T. R., et al. (1987) "Melatonin Rhythym in Human Plasma and Saliva," *Journal of Pineal Research* 4(1987): 177-183.

Mahal, H. S., Sharma, H. S. and Mukherjee, T. (1999). "Antioxidant properties of Melatonin: A pulse radiolysis study." *Free Radical Biology & Medicine*, 26(5/6): 557-565

Touitou, Y. (2001) "Human aging and melatonin. Clinical relevance" *Experimental Gerontology* 36 (2001): 1083-1100.

Tran, H. T. T., Tran, P. H. L. and Lee, B.-J. (2009) "New findings on melatonin absorption and alterations by pharmaceutical excipients using the Ussing chamber technique with mounted rat gastrointestinal segments" *Int. J Pharmaceutics* 378 (2009): 9-16.

What is claimed is:

1. A controlled-release melatonin product comprising:
    a composition comprising melatonin, a pH lowering agent, and a gel-forming forming polymer that, when said composition is ingested, forms an aqueous gel matrix having melatonin dissolved therein and an internal pH of 2-4 in said aqueous gel matrix, wherein:
    said composition provides a first release dose of melatonin for assisting in inducement of sleep and a subsequent sustained release dose of melatonin for assisting in sustaining sleep; wherein:
    said first release dose of melatonin is 50% of the melatonin within 1-3 hours after ingestion; and
    said sustained release dose of melatonin is 50% to 90% of the remaining melatonin within 3-9 hours after ingestion.

2. The product of claim 1, wherein said composition is in a tablet dosage form, multiparticulate-containing dosage form, or a combination thereof.

3. The product of claim 1, wherein said composition is effective to release substantially all of the remaining melatonin in said composition into the gastrointestinal tract within ten hours after oral ingestion.

4. The product of claim 1, wherein said composition is effective to release substantially all of the remaining melatonin in said composition into the lower gastrointestinal tract within ten hours after oral ingestion.

5. The product of claim 1, wherein said pH lowering agent is an acid, acidic buffer, or a combination thereof.

6. The product of claim 1, wherein said composition further comprises at least one other active ingredient in addition to said melatonin.

7. A controlled-release melatonin product comprising:
    a compressed tablet comprising melatonin, citric acid, microcrystalline cellulose, and a hydroxypropyl methylcellulose that after ingestion to form an acidic hydrogel that dissolves said melatonin and is effective to provide a first release dose of melatonin for assisting in inducement of sleep and a subsequent sustained release dose of melatonin for assisting in sustaining sleep while in a human subject's gastrointestinal tract, the amount of citric acid being sufficient to impart a pH of 2-4 to said hydrogel; wherein:

said first release dose of melatonin is 50% of the melatonin within 1-3 hours after ingestion; and
said sustained release dose of melatonin is 50% to 90% of the remaining melatonin within 3-9 hours after ingestion.

8. The product of claim 7, wherein said tablet is effective to release substantially all of the remaining melatonin in said tablet into said human subject's gastrointestinal tract within ten hours after oral ingestion.

9. The product of claim 7, wherein said tablet is effective to release substantially all of the remaining melatonin in said tablet into said human subject's lower gastrointestinal tract over within ten hours after oral ingestion.

10. The product of claim 7, wherein said tablet further comprises at least one other active ingredient in addition to said melatonin.

11. A sleep-aid product comprising:
a sleep-aid effective amount of a composition comprising melatonin, a gel-forming polymer, and a sufficient amount of at least one acidic moiety to impart a pH of 2-4 to said gel-forming polymer after oral ingestion by a human subject;
said gel-forming polymer and acidic moiety are effective to form a gel matrix having said pH when said composition is in said human subject's intestines for solubilizing said melatonin within said gel matrix; wherein:
said composition is effective to release 50% of said melatonin in said composition into said human subject's gastrointestinal tract within 1-3 hours after oral ingestion; and
said composition is effective to release 50% to 90% of the remaining melatonin within 3-9 hours after ingestion.

12. The product of claim 11, wherein said composition is effective to release approximately 50% of said melatonin in said composition into said human subject's gastrointestinal tract within approximately two hours after oral ingestion.

13. The product of claim 11, wherein said composition further comprises at least one other active ingredient in addition to said melatonin.

14. The product of claim 11, wherein said sleep-aid effective amount includes 5 micrograms to 10 milligrams of said melatonin.

15. The product of claim 11, wherein said composition is in a tablet dosage form, multiparticulate-containing dosage form, or a combination thereof.

16. The product of claim 11, wherein said composition is effective to release substantially all of the remaining melatonin in said composition into said human subject's gastrointestinal tract within approximately ten hours after oral ingestion.

17. The product of claim 11, wherein said composition is effective to release substantially all of the remaining melatonin in said composition into said human subject's lower gastrointestinal tract within ten hours after oral ingestion.

18. The product of claim 11, wherein an amount of said acidic moiety is sufficient to maintain said pH for at least 7 hours.

19. The product of claim 11, wherein said acidic moiety is an acid, acidic buffer, or a combination thereof.

20. The product of claim 11, wherein said acidic moiety is an organic acid.

* * * * *